United States Patent
Vasan et al.

(10) Patent No.: US 9,151,723 B2
(45) Date of Patent: Oct. 6, 2015

(54) 3D RF MEMS BIOSENSOR FOR MULTIPLEXED LABEL FREE DETECTION

(71) Applicant: Oxfordian, LLC, Dallas, TX (US)

(72) Inventors: Arvind Sai Sarathi Vasan, College Park, MD (US); Michael G. Pecht, Hyattsville, MD (US); Andrew Michael Kluger, San Rafael, CA (US)

(73) Assignee: OXFORDIAN, LLC, Dallas, TX (US)

( * ) Notice: Subject to any disclaimer, the term of this patent is extended or adjusted under 35 U.S.C. 154(b) by 0 days.

(21) Appl. No.: 13/986,566

(22) Filed: May 15, 2013

(65) Prior Publication Data

US 2014/0011697 A1     Jan. 9, 2014

Related U.S. Application Data

(60) Provisional application No. 61/688,509, filed on May 16, 2012.

(51) Int. Cl.
| | |
|---|---|
| *G01N 33/543* | (2006.01) |
| *G01N 27/22* | (2006.01) |
| *G01N 33/569* | (2006.01) |
| *G01N 27/327* | (2006.01) |

(52) U.S. Cl.
CPC .......... *G01N 27/22* (2013.01); *G01N 27/3275* (2013.01); *G01N 33/5438* (2013.01); *G01N 33/56933* (2013.01)

(58) Field of Classification Search
None
See application file for complete search history.

(56) References Cited

U.S. PATENT DOCUMENTS

| | | | |
|---|---|---|---|
| 7,993,854 B2 | 8/2011 | Mutharasan et al. | |
| 2004/0197227 A1* | 10/2004 | Hauan et al. | 422/58 |
| 2009/0320606 A1* | 12/2009 | Carlen et al. | 73/718 |
| 2010/0088039 A1 | 4/2010 | Yang et al. | |

FOREIGN PATENT DOCUMENTS

WO    WO 2011060184 A1 *  5/2011  ............... C12M 3/00

OTHER PUBLICATIONS

Kim et al. (2006) "Biosensors for label free detection based on RF and MEMS technology" Sensors and Actuators B 119:592-599.*
Rong Fan, et al., Integrated barcode chips for rapid, multiplexed analysis of proteins in microliter quantities of blood, Nature Biotechnology, vol. 26, No. 12, pp. 13.

* cited by examiner

*Primary Examiner* — Tracy Vivlemore
*Assistant Examiner* — Karen S Weiler
(74) *Attorney, Agent, or Firm* — Lawrence Edelman; The Law Office of Lawrence Edelman

(57) ABSTRACT

A label-free RF MEMS-based biosensor is described for detecting biomarkers in a given environment. The biosensor is capable of sensing the presence of biomarkers by exploiting both its mechanical and electrical characteristics. In addition, the method employed for detecting mechanical deflections due to antigen-antibody binding uses a simple electrical circuitry which allows the sensor to be used at any location and time. Such a sensor, when placed in a matrix like structure allows for the detection of multiple biomarkers simultaneously.

8 Claims, 12 Drawing Sheets

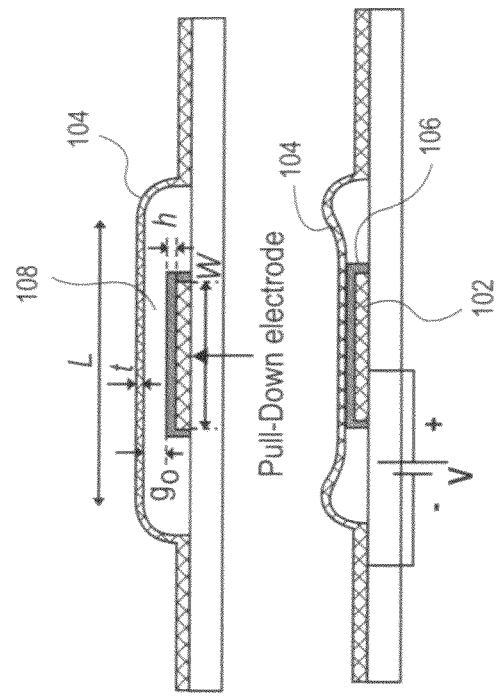
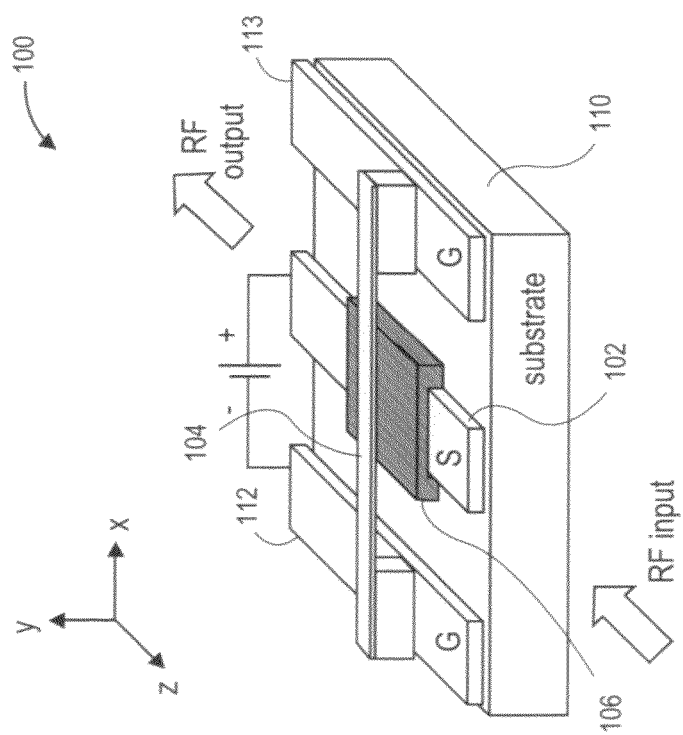
FIG. 1B
FIG. 1A

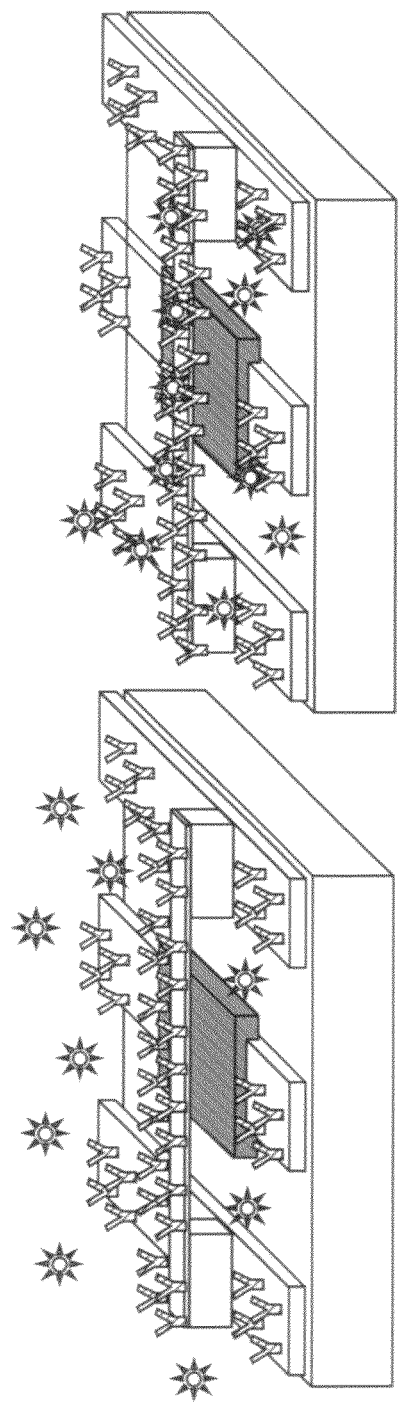

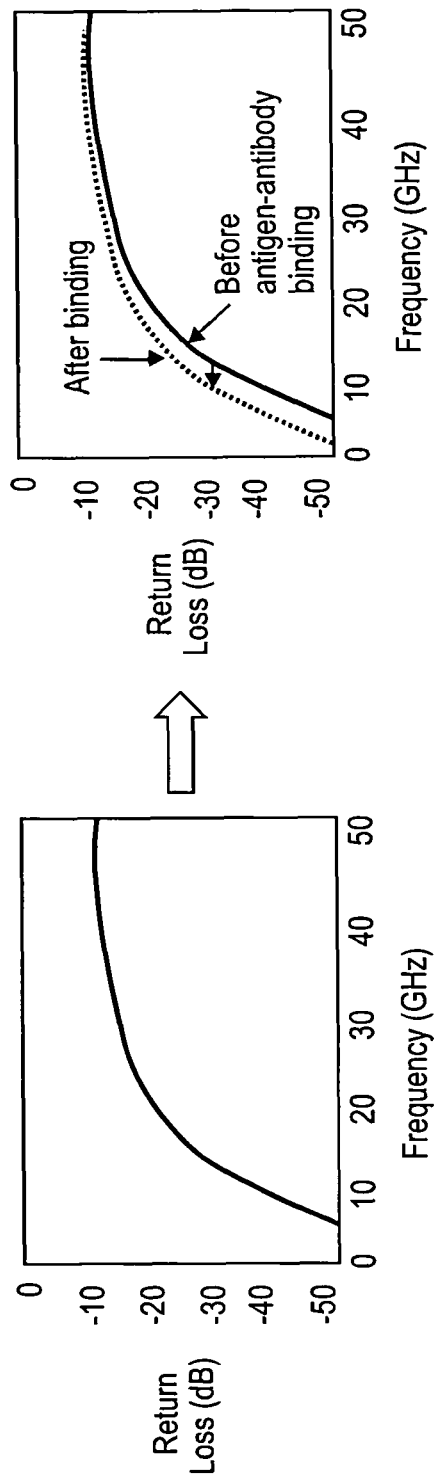

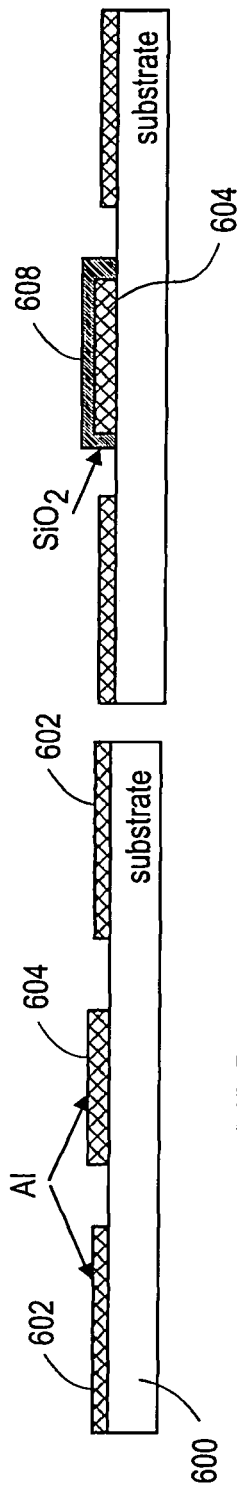
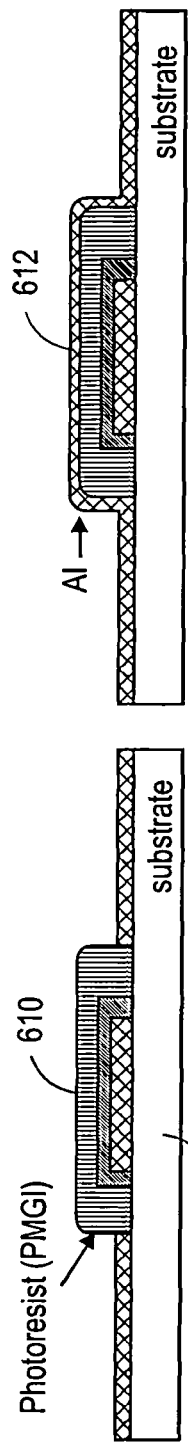
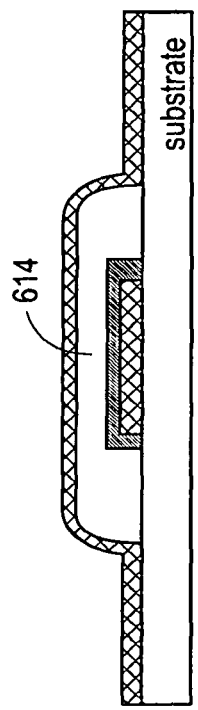
FIG. 6A
FIG. 6B
FIG. 6C
FIG. 6D
FIG. 6E

3D RF MEMS BIOSENSOR FOR MULTIPLEXED LABEL FREE DETECTION

CROSS REFERENCE TO RELATED CASE

This non-provisional patent application claims priority to U.S. Provisional Application Ser. No. 61/688,509 filed May 16, 2012, entitled Embedded 3D Biomems for Multiplexed Label Free Detection, the contents of which application is incorporated herein, as if fully set forth in its entirety.

FIELD OF INVENTION

This invention relates to a biosensor for rapid, label free, multiplexed detection of biomarkers, and more particularly to the use of an array of RF MEMS capacitors as biosensors to accomplish such detection.

BACKGROUND OF THE INVENTION

Genomics and proteomics research has elucidated many new biomarkers that have the potential to greatly improve disease diagnosis [2-3]. The development of rapid and inexpensive diagnostic assays adapted for point-of-care (PoC) applications would aid in the control of diseases [1]. The availability of multiple biomarkers is believed to be critical in the diagnosis of complex diseases like cancer [4], for which disease heterogeneity make tests of single marker inadequate. Hence, real-time detection of multiple biomarkers associated with different stages of disease pathogenesis could facilitate early detection of diseases [5]. However, widespread use of such biomarkers in disease diagnosis ultimately depends upon the development of field deployable biosensor devices. For PoC applications, biosensors are expected to allow real-time, rapid, label-free and multiplexed detection of biomarkers with high selectivity and sensitivity. Such devices would not only reduce time between sampling and responses but will also reduce costs by making tests available in environments where laboratory testing is unavailable or impractical [6].

Prevailing bio-detection systems mainly rely on fluorescence methods (label-based detection) to detect the binding of biomarkers to a biorecognition element. This includes the commonly used clinical approach for protein marker detection, enzyme-linked immunoabsorbent assay (ELISA). Though past research has demonstrated detection limits as low as few femtamolar concentrations (pg/ml) using fluorescence based detection, the need for sophisticated and costly instruments, long detection time and complicated process steps make label-based detection methods incompatible for hand-held portable biosensing applications [7]. Rapid, multiplexed, detection has not been attained with any existing label free detection schemes including surface plasmon resonance (SPR) [8-10], microcantilevers [11-14], carbon nanotubes [15-16] and quartz crystal microbalance [17]. Fan et al [18] reported an integrated microfluidic system which they called the integrated blood barcode chip (IBBC) to address the issue of multiplexed detection of protein in microliter quantities of blood. Though the chip proved to be a new approach for multiplexed immunoassays, it ultimately depends on fluorescent labels to detect the proteins of interest which makes it not suitable for portable and remote health monitoring application. A similar approach was used by Zheng et al [19] where nanowire sensor arrays were used for multiplexed electrical detection of cancer biomarkers.

Micro Electro-Mechanical Systems (MEMS) technology holds the potential to allow integrated sensors for the detection of biomarkers in hand held devices. Miniaturized sensor size aids in reducing measurement time and minimizing invasiveness. Recently, MEMS and related technologies have found interest in rapid label-free detection of biomarkers. Kim et al [20] demonstrated a detection method based on RF electric signals and MEMS to detect Glucose oxidase (GOx). Dalmay et al [21] developed a detection method using microwave frequencies to study cell electrical parameters.

SUMMARY OF THE INVENTION

By way of this invention radio frequency (RF) and MEMS technology has been exploited for the in-situ, on-chip multiplexed detection of biomarkers in the solution of interest. The immunoassay region of the chip employs a plurality of RF MEMS shunt capacitors embedded in microfluidic channels and customized for the detection of multiple biomarkers.

The approach herein involves two parallel modes of sensing (resulting in 3-D sensing) for the reliable quantification of target analyte using a single RF MEMS capacitive structure configured as a coplanar wave guide (CPW). The versatility of the RF MEMS shunt capacitive sensor is demonstrated by detecting Staphylococcus aureus (S. aureus) using monoclonal IgG3 antibodies prepared from mice. Finally a design is disclosed which integrates microfluidics with RF MEMS sensors for extending a single immunoassay to the detection of multiple biomarkers (multiplexed detection).

BRIEF DESCRIPTION OF THE DRAWINGS

The present invention is described with respect to particular exemplary embodiments thereof and reference is accordingly made to the drawings in which:

FIG. 1A is a schematic 3D representation of an RF MEMS capacitor. FIG. 1B presents a side view of the RF MEMS capacitor of FIG. 1A illustrating the deflection of the suspended membrane in response to electrostatic actuation.

FIG. 3A shows the position of suspended membrane before antigen-antibody binding and 3B shows the change in suspended membrane position due to antigen-antibody binding on the surface of the suspended membrane. FIGS. 3C and 3D are three dimensional views of the RF MEMS capacitors of FIGS. 3A and 3B.

FIG. 4A and FIG. 4B illustrate the effect on return loss of the RF MEMS capacitor due to the biomolecular interactions between the target antigen and antibody molecules on the coplanar wave guide (CPW) surface.

FIG. 6A through FIG. 6E illustrate various stages of the fabrication of an RF MEMS capacitor made according to an embodiment of the invention.

DETAILED DESCRIPTION OF THE INVENTION

Figure 2:
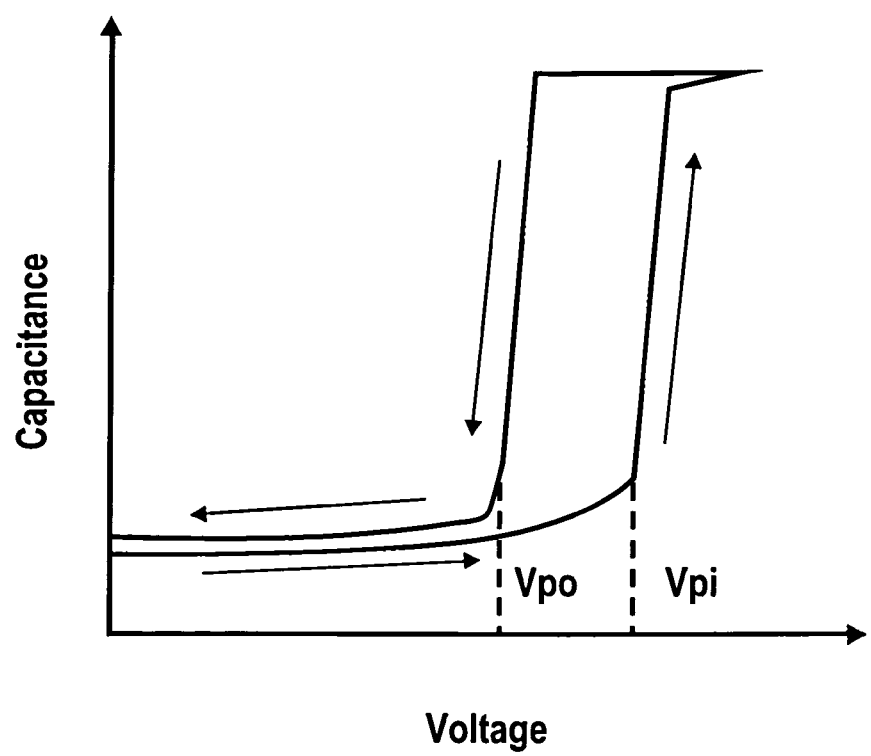
FIG. 2 is representative of a capacitance-voltage curve for a RF MEMS capacitor.
Figure 3A:
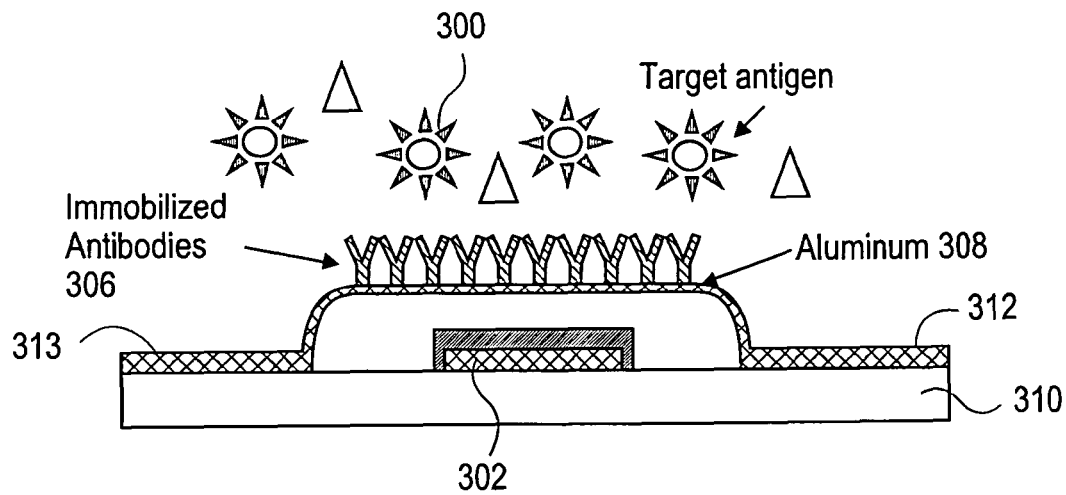
FIGS. 3A and 3B illustrate surface stress-based sensing wherein the suspended membrane in RF MEMS capacitor deflects due to the interactions between target antigens and antibody molecules on the RF MEMS membrane.
Figure 3B:
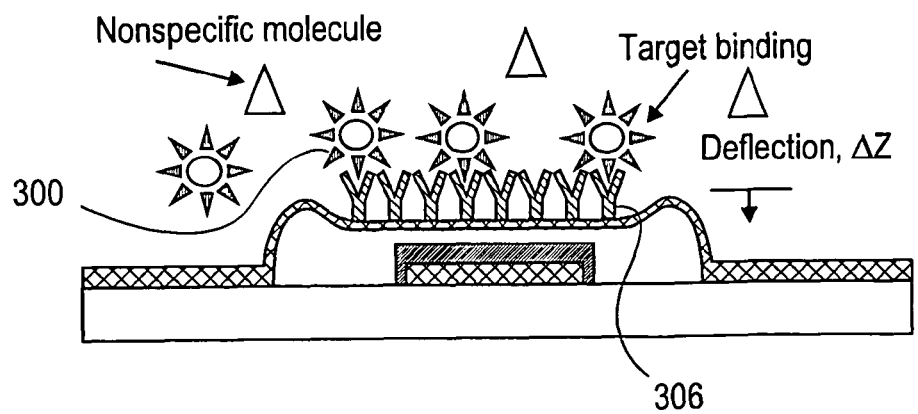

RF MEMS capacitors are electrical switches which typically use mechanical movement to achieve a switching action in the RF transmission line [22]. RF MEMS capacitive switches commonly include a thin flexible metal membrane, which is suspended across two support posts and actuated electrostatically via a stationary electrode beneath the membrane [22-24]. FIG. 1 is a schematic representation of such an RF MEMS 100. The switch comprises two electrodes including a bottom or signal line electrode 102, and a top, suspended flexible membrane electrode 104. In the embodiment shown the suspended flexible membrane is oriented perpendicular to the direction of signal line 102. Switch 100 is disposed upon a substrate 110, said substrate usually made out of a material such as Silicon (Si). Conductive ground lines 112 and 113 usually made out of Aluminum (Al), complete the structure. The ground lines (112 and 113) along with the signal line (102) forms a coplanar waveguide (CPW) structure. The top electrode 104 can be pulled down by applying a voltage across the air gap 108 between the two electrodes (ground and signal lines). Above a certain voltage, the balance between the attracting electrostatic force and restoring spring force becomes unstable and the switch closes i.e. the suspended membrane deflects towards the signal line (see FIG. 1B). This voltage at which switch closes is called the pull-in voltage (Vpi). A dielectric layer 106 usually made out of materials like $SiO_2$ prevents electrical short between the ground and signal line. Once closed, the electric forces are much higher due to the shorter distance between the electrodes, and the switch will only open again if the voltage is lowered beneath the so-called pull-out voltage (Vpo). Due to the presence of dielectric (air and $SiO_2$) between the signal line and the suspended membrane, the switch essentially behaves like a capacitive switch. Exemplary of the resulting C-V curve during switching action is shown in FIG. 2.

The conversion of RF MEMS shunt capacitors into biosensors for biomarker detection is carried out by immobilizing antibodies (a biorecognition element) to the membrane and CPW (formed using the ground and signal line topology shown in FIG. 1A) surfaces. Label free detection of biomarkers using RF MEMS capacitors can be achieved using two parallel modes of sensing, namely (i) surface stress based detection and (ii) RF losses based detection. The principle of bio-detection in the surface stress mode relies upon the fact that when specific biomolecular binding occurs on one surface of the membrane or deflecting beam, changes in intermolecular nanomechanics results in flexing of the membrane [11]. This flexural movement changes the capacitance across the RF MEMS switch. In the RF loss detection mode, a small pattern or material change in the CPW transmission line causes large changes in the RF impedance characteristics [20]. By calibrating and monitoring the change in RF characteristics, biosensing action is realized.

Surface Stress Based Detection

FIGS. 3A-3D illustrate the surface stress mode of sensing using an RF MEMS structure. When no biomarkers 300 are present, and no voltage bias is applied across signal line 302 and ground lines 312 and 313, the suspended membrane remains in the open position. This is because the weight of antibodies 306 are (~0.25 Daltons for IgG3) negligible when compared with the weight of the suspended membrane 308 (for 100×250 μm2~67.5 μgm) and thus the membrane does not experience any flexural force. When the biomarkers 300 bind with antibodies 306, the top electrode (suspended membrane) experiences a flexural force resulting in the bending of membrane and thus increases the capacitance across signal line 302 and the membrane 308. The amount of membrane deflection or bending depends on the amount of antigen-antibody binding on the membrane surface.

The membrane deflection originates from the change in surface free energy (Δσ) of the surface coated with biorecognition molecules. Because specific binding between the biomarker and biorecognition molecules leads to much higher free-energy change than for nonspecific binding, membrane deflections are a response to specific binding [11][26]. The increase in capacitance across signal line 302 and the membrane 308 can be found by applying an appropriate voltage bias and using an appropriate electrical circuitry.

Referring back to FIG. 1 it can be seen that surface stress based detection is confined to sensing in the y-direction.

RF Loss Based Detection

The theory behind label free bio-detection method based on RF signal is the skin effect i.e. concentration of electrons on the surface of a transmission line. In RF transmission lines, the signal power is concentrated on the surface of the line and accounts for insertion and return loss. If biomolecules with electrical properties such as proteins which possess static charges [20] accumulate at the RF micro stripe line (for example as illustrated in FIGS. 3C and 3D), then the RF characteristics of the transmission line changes. The change in RF characteristics can be measured from the change in S-parameters, phase shift and signal attenuation. For example, the reflection coefficient $|S_{11}|$, of a shunt-capacitive switch is directly proportional to the capacitance of the switch, $C_u$ expressed as $$|S_{11}|^2 = \frac{\omega^2 C_u^2 Z_0^2}{4} \qquad (1)$$

where $C_u$ is the capacitance of the switch. However, the accumulation of biomolecules changes the capacitance. This in turn changes the reflection coefficient of the RF MEMS capacitive switch. Also, the losses arise from conductance dissipation. The conductance loss factor $\alpha_c$ is evaluated from $$\alpha_c(Np/m) = \frac{R_s}{2Z_0 I^2}\int_{-a}^{+a} J_s^2\, dx + 2\int_{b}^{b_{max}} J_{gp}^2\, dx \qquad (2)$$

where $J_s$ depends on the longitudinal current linear density ($J_s$) of the CPW, the ground-plane current linear density ($J_{gp}$), the characteristic impedance of the CPW, the total ground-plane current, and the metal surface resistivity (equation 2 referred from reference [20]).

In bio-detection, the biomolecules can be considered as small conductive materials having a low conductivity. The presence of these molecules on the CPW surface changes the characteristic impedance and the current density of the transmission line. This in turn results in the dissipation from the conductive surface, thereby contributing to RF losses. The conductance dissipation mainly depends on the number of molecules immobilized on the CPW and membrane surface. In FIG. 4 the RF-loss based sensing, wherein effect on return loss of the RF MEMS capacitor due to the biomolecular interactions between the target antigen and antibody molecules on the coplanar wave guide surface (CPW) is shown. In RF loss-based sensing mode, changes in RF characteristics are accounted for due to the antigen-antibody binding along the CPW (x and z-direction). Thus, the two parallel modes (surface stress-based and RF-loss-based sensing) utilize all the 3-dimensions of RF MEMS structure for sensing.

RF MEMS Design

Figure 5:
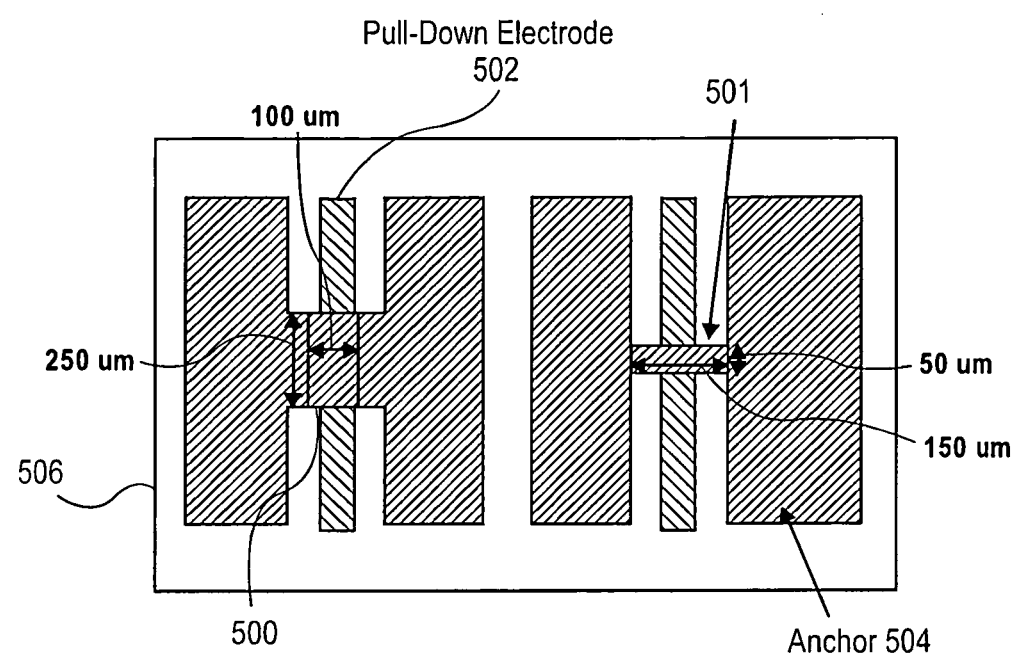
FIG. 5 is a top down view of the exemplary RF MEMS capacitors used in the experiments described in the Detailed Description of the Invention to demonstrate label-free detection.

The geometry of an exemplary shunt capacitive metal membrane switch is shown in FIG. 5. The switch is based on a fixed (Al) membrane 500, and 501 bridged over a silicon dioxide (SiO2) film 502 deposited on top of the bottom Al electrode (signal line, not shown as it is covered by the SiO2 film). The anchors 504 (i.e. the ground lines) are connected to the CPW ground plane 506, and the membrane is, therefore grounded. When an electrostatic potential is applied between the membrane and the bottom electrode 502, the attractive electrostatic force pulls the metal membrane 500, 501 down onto the bottom dielectric 502. The dielectric film serves to prevent contact between the two metallic surfaces, yet provides a low impedance path between them. When the membrane is not actuated, the air between the two contacts exhibits a low capacitance, given by [24][27]

$$C_{off} = \frac{1}{(h/\varepsilon_D A) + (g_0/\varepsilon_a A)} \quad (3)$$

where $C_{off}$ is the capacitance of the switch in the off state, $\varepsilon_D$ and $\varepsilon_a$ the dielectric constants of dielectric material (SiO$_2$) and air, respectively, h the dielectric layer thickness, $g_0$ the air gap between the membrane and the dielectric layer, and A the overlap area between the bottom electrode and the membrane. When the switch is actuated, the metal-dielectric-metal sandwich possesses a significant capacitance, $C_{on}$ described by $$C_{on} = \frac{\varepsilon_D A}{h} \quad (4)$$

Table I and II lists the physical features and dimensions of an exemplary MEMS microwave switch (which may be used according to certain aspects of the invention) used in the feasibility study.

TABLE I

Physical Dimensions of the RF MEMS shunt capacitor

| Component | Material | Dimension |
|---|---|---|
| MEMS bridge | Aluminum | t = 1 μm, w = width, L = length |
| Signal line | Aluminum | thickness = 1 μm, W = 50 μm |
| Dielectric layer | SiO$_2$ | h = 1 μm, $\varepsilon_D$ = 3.9 |
| Air gap | Air | $g_0$ = 1.7 μm |
| Gap between Ground and Signal line | Air | 25 μm |

TABLE II

Mechanical and electrical properties of the designed RF MEMS

| w × L (μm$^2$) | Stiffness (N/m) | $V_{pi}$ (volts) | $C_{on}$ (pF) | $C_{off}$ (pF) | $C_{ratio} = C_{on}/C_{off}$ |
|---|---|---|---|---|---|
| 250 × 100 | 564.08 | 30.84 | 0.86 | 0.113 | 7.62 |
| 50 × 100 | 112.81 | 30.84 | 0.17 | 0.026 | 6.58 |

RF MEMS Fabrication

RF MEMS switches were fabricated using the dimensions listed in Table 1. As shown in FIG. 6 (A), the device fabrication process begins with the deposition and patterning of aluminum (1 μm) onto a wafer substrate 600 to form the ground lines 602 and signal line 604 of the CPW (W=50 μm, G-S-G=25 μm). A 1 micron, nano-porous SiO2 dielectric isolation layer 608 which separates the membrane 612 and signal line 604 was deposited and then wet etched at appropriate places to produce the structure illustrated at FIG. 6B. A sacrificial photoresist layer 610 was then spin coated and patterned to define the air gap 614 (1.7 μm) between the dielectric layer 608 and the to be deposited top membrane 612, resulting in the structure of FIG. 6C, and FIG. 6D respectively. The metal membrane was fabricated using aluminum because of its high resistance to fatigue and low electrical resistance. This was followed by the removal of the photoresist mold using acetone to release the membrane, the final product illustrated at FIG. 6E.

Experimental Protocol

Signal Readout

Figure 7:
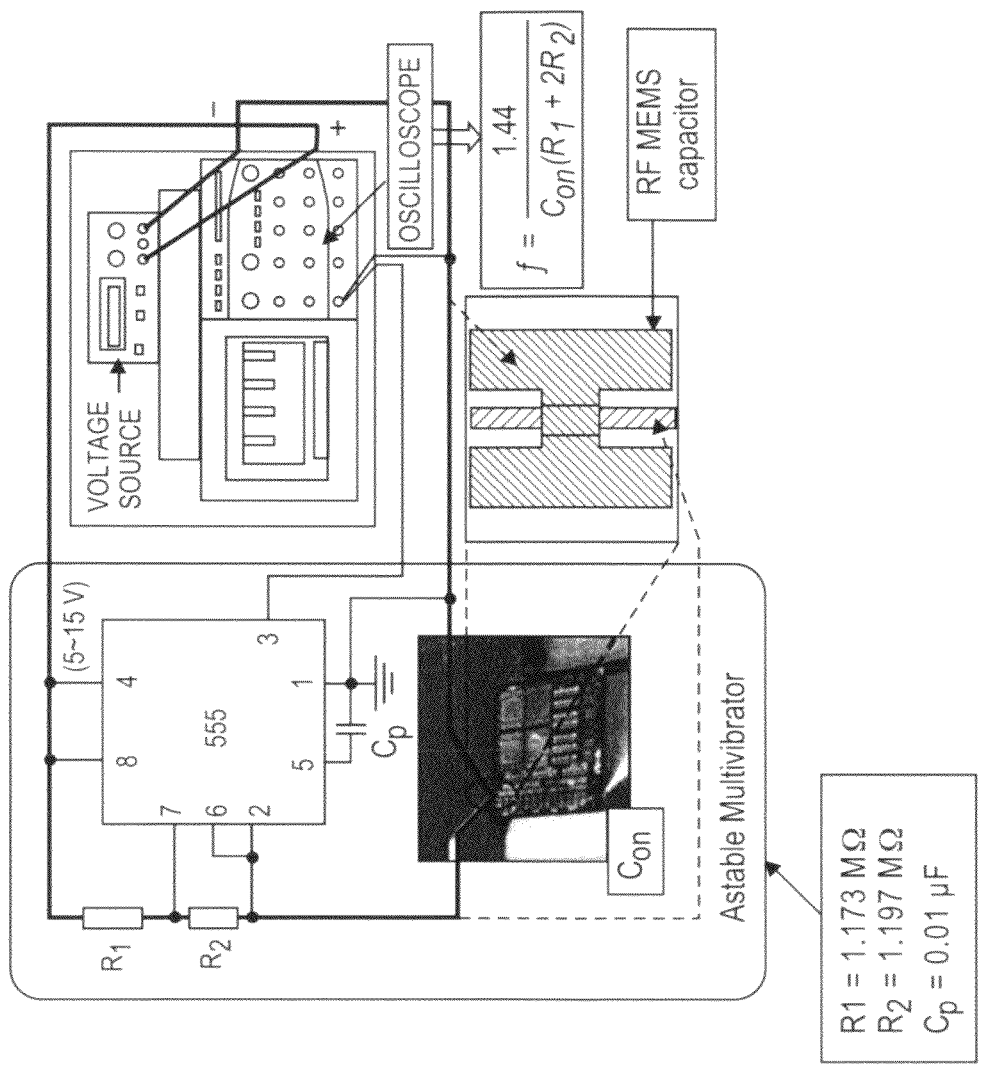
FIG. 7 is a schematic representation of an exemplary astable multivibrator circuit that can be used for detecting capacitance changes in the RF MEMS capacitor due to membrane deflection as a result of antigen-antibody binding.

A schematic of the experimental setup used to sense the change in capacitance of the RF MEMS due to antigen-antibody binding is given in FIG. 7. An astable multivibrator circuit (any capacitive sensing circuit could be employed) was designed to indirectly observe the low value of capacitance offered by the RF MEMS from the frequency of the output signal. In order to verify the feasibility of RF MEMS for stress based sensing, the change in time duration (frequency) of the astable multivibrator output signal due to the change in up-state capacitance of the RF MEMS illustrated at FIG. 5 (w=250 μm, L=100 μm and w=50 μm, L=150 μm) was monitored at a digital oscilloscope. The output frequency (or time duration) of the astable multivibrator circuit is controlled by a timing capacitor, which in this context is the RF MEMS capacitor. The astable multivibrator's output signal frequency is indirectly proportional to the capacitance offered by the RF MEMS capacitor, $f=1.44*(RC)^{-1}$.

In the astable operation, the trigger terminal (2) and the threshold terminal (6) are connected so as to form a self-trigger, causing the 555 timer to operate as a multivibrator. Here, $R_1$ and $R_2$ act as timing resistors and the discharge pin is connected to the junction of $R_1$ and $R_2$. When the supply $v_{cc}$ is connected, the RF MEMS capacitor C acts like a timing capacitor and changes towards $V_{cc}$ with a time constant $(R_1 + R_2) \cdot C$. When the capacitor gets charged the output (3) is held high. When the timing capacitor voltage is just greater than $(2/3)v_{cc}$, the upper comparator of the 555 timer triggers the internal control flip flop and the capacitor discharges towards the ground through $R_2$ with a time constant $R_2 \cdot C$. During this discharge cycle the output is held low. During the discharge of the timing capacitor C, as the voltage across C reaches $(1/3)v_{cc}$ the lower comparator is triggered and again it starts charging and the output is held high. Thus the capacitor is periodically charged between $(1/3)v_{cc}$ and $(2/3)v_{cc}$. The length of time that the output remains high is the time for the capacitor to charge from $(1/3)v_{cc}$ and $(2/3)v_{cc}$ and this is given by $T_h=0.693 \cdot (R_1+R_2) \cdot C$. The discharge cycle is expressed as $T_1=0.693 \cdot R_2 \cdot C$. Thus the frequency of the output signal from an astable multivibrator is given by $$f = \frac{1}{T} = \frac{1}{T_h + T} = \frac{1.44}{(R_1 + R_2) \cdot C} \quad (5)$$

Thus, when antigen-antibody binding takes place at the suspended membrane of the RF MEMS capacitor, the capacitance offered by the capacitor increase, thereby increasing the time period (or decreasing the frequency) of the astable multivibrator output.

Test Procedure

Cleaning Procedure.

The RF MEMS chip was sequentially cleaned with acetone, methanol and isopropanol for 14 hrs, 2 hrs and 30 mins respectively. At each stage the RF MEMS chip was rinsed with deionized water for 10 mins. This process was done immediately before the experiments. The time period of the astable multivibrator output signal was measured by using RF MEMS (without antibody-antigen binding) as the timing capacitor.

Immobilization.

RF MEMS were directly coated with 0.1 µL of 100 µg/mL S. aureus mouse monoclonal IgG3 antibody and incubated at 4° C. for 2 hrs. 4 µL of 10 mg S. aureus (wood strain without protein A) bio-particle fluorescein conjugate was suspended and purified three times with 25 µL PBS solution using micro centrifuge. After immobilizing the antibody, a purified solution of S. aureus was then injected on the RF MEMS structures. Sufficient time (4 hrs) was provided for the bacteria and antibody to react. Excess unbound S. aureus were removed by rinsing the sample three times with PBS solution. The RF MEMS coated with antibodies and antigen was studied by monitoring the change in time period of the astable multivibrator output using the coated RF MEMS as timing capacitor.

Since, in this experiment only a feasibility study was conducted, no surface modification techniques were employed. However, the sensitivity of this RF MEMS biosensor can be improved by employing surface modification techniques such as with silane chemistry or thiol chemistry.

Results.

Figure 8A:
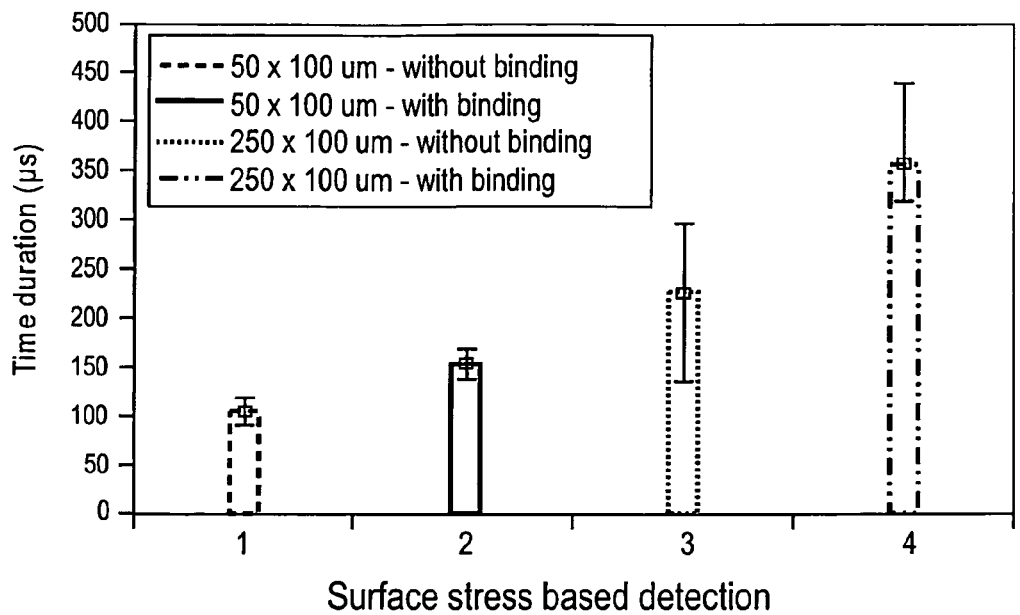
FIG. 8A shows the result for stress-based sensing wherein the change in the time period of the astable multivibrator output signal before and after antigen-antibody binding is plotted with different membrane geometries.

FIG. 8A shows the change in time duration of the astable multivibrator output with RF MEMS capacitor (with and without antigen-antibody binding) as the timing capacitor. The membrane dimensions used in the experiments were 250 and 50 µm wide, and 100 and 150 µL long, respectively. With S. aureus-IgG3 antibody immobilized on the surface of Al membrane, the membrane was found to bend as a result of antigen-antibody binding, irrespective of the membrane dimension. This is caused by the increased intermolecular repulsion between the antigen-antibody complexes on the membrane surface. This deflection was confirmed by the increase in time period of the astable multivibrator output (due to increase in capacitance of the RF MEMS capacitor).

When there is no antigen—antibody binding, the existence of output signal is accounted for by the presence of parasitic capacitance. It should be noted that the astable circuit was not optimized (i.e. calibrated) to bio-detection and was used only to demonstrate feasibility.

Figure 8B:
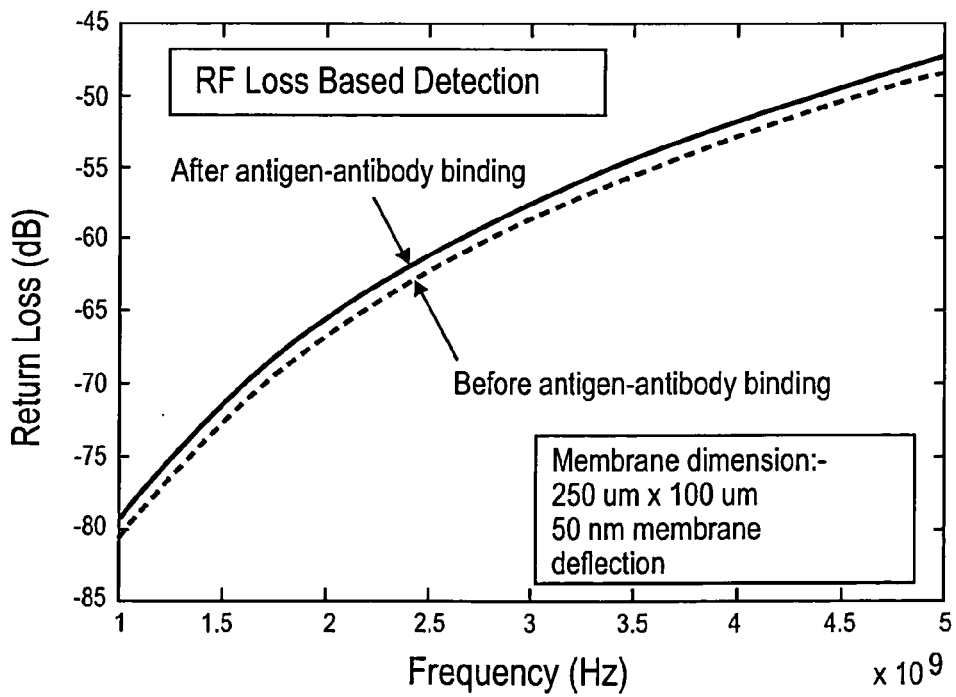
FIG. 8B shows the simulation results for RF loss-based sensing wherein the change in the return loss characteristics of the RF MEMS capacitor is plotted for a membrane deflection of 50 nm resulting from antigen-antibody binding.

In order to validate the RF MEMS ability for bio-detection using RF signal losses, a simulation study was carried out which assumed membrane deflection was due to antibody-antigen binding using Equation (1). Given the RF MEMS configuration where w=250 µm, L=100 µm, the return loss characteristics ($RL(dB)=20 \log_{10}|S_{11}|$) the result of the simulation are plotted in FIG. 8B. From this plot it can be seen that the presence of antigen-antibody binding on the RF MEMS CPW surface results in an increase in input return loss of the RF MEMS shunt capacitor.

Multiplexed Detection Using Embedded MEMS

Principle of Multiplexed Detection

The principle behind multiplexed detection of biomarkers using RF MEMS capacitors follows the idea suggested by Fan et al. [18]. Instead, however, by way of the present invention multiple RF MEMS sensors are used instead of DNA-encoded antibody libraries. The use of RF MEMS capacitors as biosensors allows for label-free detection which is not the case in the biosensing method employed by Fan et al. [18]. The use of fluorescence based biosensing technique by Fan et al [18], confines their sensor for use within a laboratory setting. However, the label-free detection characteristic of the RF MEMS capacitors enables them to perform rapid, label-free, multiplexed detection irrespective of location and time.

Figure 9:
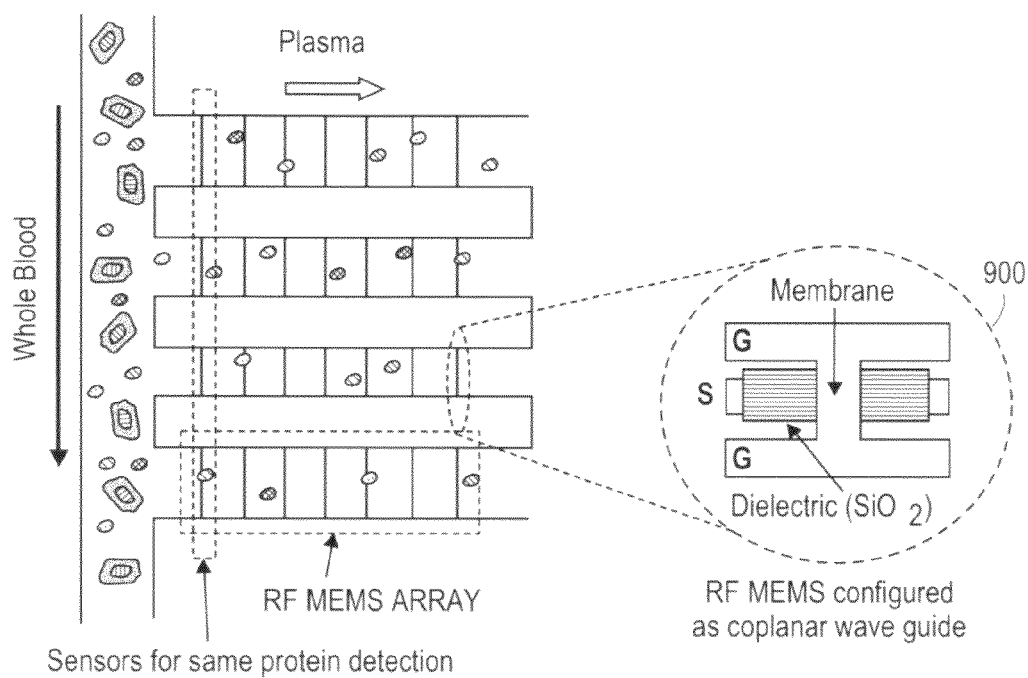
FIG. 9 is a schematic illustration of a multiplexed detection system according to an embodiment of the invention using RF MEMS capacitive biosensors embedded in microfluidic channels.

FIG. 9 shows a schematic depicting a device for multiple biomarker detection using multiple RF MEMS capacitors 900 integrated into microfluidic channels. In Fan et al [18] a microscopic barcode array of single-stranded DNA (ssDNA) oligomers is employed. By way of distinction, in exemplary embodiments of the present invention, the immunoassay region comprises a multiplicity of surface modified RF MEMS capacitors electrically connected to other RF MEMS capacitors of the same type in parallel microfluidic arms. Here, by same type, we refer to RF MEMS sensors immobilized with same type of antibody (for detecting the same antigen in parallel fluidic arms).

Figure 10A:
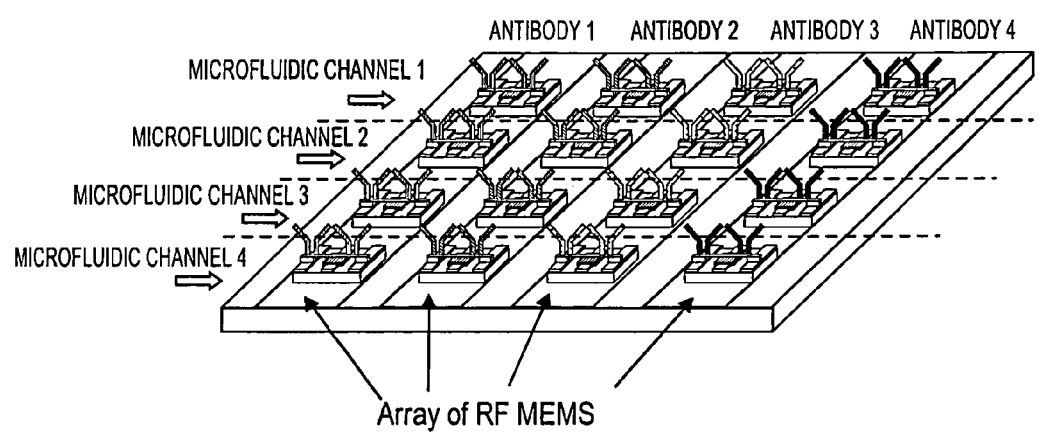
FIG. 10A is a 3D schematic illustration of a matrix of RF MEMS capacitive biosensors embedded onto an integrated microfluidic chip for multiplexed detection according to an embodiment of the invention.
Figure 10B:
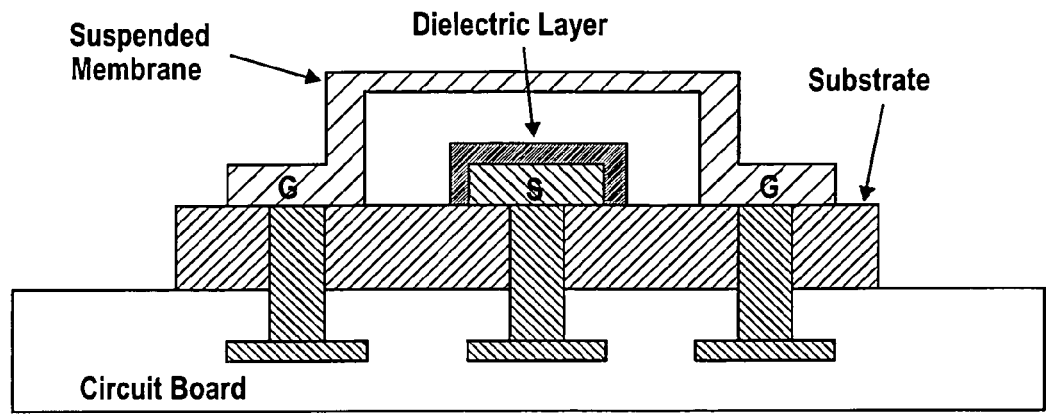
FIG. 10B depicts an exemplary circuit board connection for a single RF MEMS capacitor illustrated in FIG. 10A.
Figure 10C:
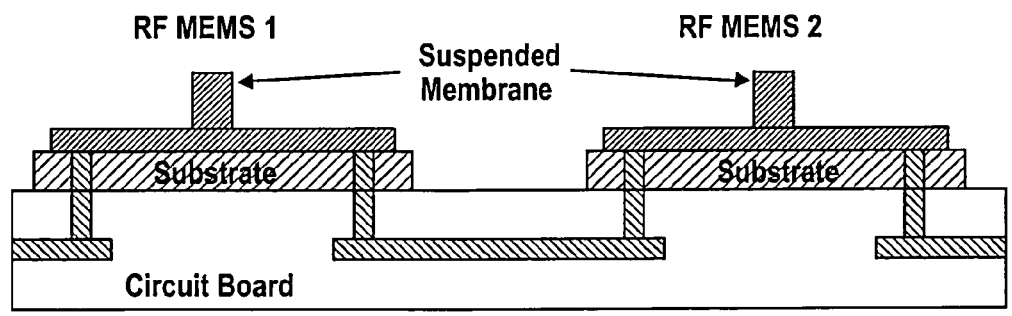
FIG. 10C depicts an exemplary circuit board connection between adjacent RF MEMS structures in a given column of the array depicted in FIG. 10A.

FIG. 10A is a three dimensional schematic of arrays of RF MEMS sensors, similar to that of FIG. 9, illustrating an exemplary arrangement of RF MEMS sensors embedded into a microfluidic chip for in situ biomarker measurement. Sample separation (in this illustration it can be thought of as blood) is realized (as in Fan et al [18]) by allowing the sample to flow through a low-flow-resistance primary channel with high resistance, while plasma is skimmed into channels that branch off at right angles with the primary channel.

As the resistance ratio is increased between the branches and the primary channel (FIG. 9), a critical streamline moves closer to the primary channel wall adjoining the branch channels. For example when blood is used as the sample, blood cells with radius larger than the distance between the critical streamline and the primary channel wall are directed away from the high-resistance channels and some of the plasma is skimmed into the high-resistance channels [18][31]. The remaining blood is directed towards a waste outlet. The plasma-skimming channels are patterned with an array of RF MEMS capacitors with immobilized antibodies. RF MEMS of the same position in parallel channels are connected in series and constitutes an array, wherein each RF MEMS capacitor is immobilized with antibody of the same kind thereby constituting one complete assay.

Design of RF MEMS Embedded Microfluidic Chip

Initially, a matrix of RF MEMS shunt capacitors can be fabricated using the process discussed earlier for the fabrication of the individual RF MEMS shunt capacitor. Next, each RF MEMS array is immobilized using microchannel-guided flow patterning methods. Here, a PDMS mold containing parallel microfluidic channels, with each channel conveying a different antibody can be used to coat RF MEMS structures at the same position in the parallel channels. To measure a large panel of biomarkers from a small quantity of a sample solution, the PDMS mould containing parallel microfluidic channels, is bonded in a direction perpendicular to the RF MEMS array. When the solution containing biomarkers flows over the RF MEMS structures, the biomarkers in the solution of interest bind to corresponding antibodies resulting in surface stresses at the RF MEMS membrane, and as well RF signal characteristic changes. Surface stress measurements are made across each capacitor and RF signal loss characteristics are measured across each RF MEMS array.

Thus, by way of this invention a new device is provided, with RF MEMS structures integrated inside the microfluidic channels, for multiplexed detection, i.e. an embedded RF MEMS integrated microfluidic chip. Notably, it is to be appreciated that the RF MEMS design described has not been optimized for bio-detection. None the less, detectable differences in capacitance and RF characteristics were able to be obtained after IgG3 treatment with *S. aureus*.

CONCLUSIONS

Rapid detection of multiple biomarkers profiles at the point-of-care will help provide necessary information pertaining to the pathological conditions associated with human diseases. Further, real time detection can facilitate early detection of potentially fatal events. By way of this invention a device is provided for the label-free, real-time multiplexed detection of biomarkers using a distributed RF MEMS embedded microfluidic chip to address the need for hand held biosensor devices that integrate sample separation with rapid in situ measurements of multiple biomarkers. The immunoassay is performed using RF MEMS capacitors that are configured as CPW. By combining parallel modes of sensing, i.e. surface stress based detection with RF signal loss detection more reliable quantification of biomarker concentrations can be realized. In addition, the devices of this invention provide an inherent advantage: parallel sensing modes, whereby valuable information about biomarker concentration based on RF signal loss detection can be obtained even if surface stress data cannot be recovered due to failure (such as by fatigue of the deflection membrane.

The multiplexed detection method described herein holds potential for inexpensive, noninvasive and informative clinical diagnoses. This is especially so because such a device can be mass fabricated, and the signal readout techniques employed avoid the need for the sophisticated instruments required for measuring the transduced signal. Also, the non-invasive sensing feature of the device of this invention simplifies the usage of the biosensor for PoC detection. Hence, this device holds special potential for next generation point-of-care services, including the coupling with wireless modules for remote health monitoring.

REFERENCES

[1] Chika Okafor, Daniel Grooms, Evangelyn Alocilja, and Steven Bolin, "Fabrication of a novel Conductometric biosensor for detecting Mycobacterium avium subsp. Paratuberclosis antibodies," Sensors, Vol. 8, pp. 6015-6025, 2008.

[2] Chris Sander, "Genomic Medicine and the Future of Health Care," Science, New Series, Vol. 287, No. 5460, pp. 1977-1978, Mar. 17, 2000.

[3] Huntington F. Willard, Misha Angrist, Geoffrey S. Ginsburg, "Genomic Medicine: Genetic Variation and Its Impact on the Future of Health Care," Philosophical Transactions: Biological Sciences, Vol. 360, No. 1460, pp. 1543-1550, Aug. 29, 2005.

[4] Steven A. Soper, Kathlynn Brown, Andrew Ellington, Bruno Frazier, Guillermo Garcia-Manero, Vincent Gau, Steven I. Gutman, Daniel F. Hayes, Brenda Korte, James L. Landers, Dale Larson, Frances Ligler, Arun Majumdar, Marco Mascini, David Nolte, Zeev Rosenzweig, Joseph Wang and David Wilson, "Point-of-care biosensor systems for cancer diagnostics/prognostics," Biosensors and Bioelectronics, Vol. 21, pp. 1932-1942, 2006.

[5] Ruth Etzioni, Nicole Urban, Scott Ramsey, Martin McIntosh, Stephen Schwartz, Brian Reid, Jerald Radich, Garnet Anderson and Leland Hartwell, "The case of early detection," Nature Reviews Cancer, Vol. 3, pp. 243-252, 2003.

[6] B. N. Feltis, B. A, Sexton, F. 1. Glenn, M. J. Best, M. Wilkins and T. J. Davis, "A hand-held surface plasmon resonance biosensor for the detection of ricin and other biological agents," Biosensors and Bioelectronics, Vol. 23, pp. 1131-1136, 2008.

[7] James F. Rusling, Challa V. Kumar, J. Silvio Gutkind and Vyomesh Patel, "Measurement of biomarker proteins for point-of-care early detection and monitoring of cancer," Analyst, VOl. 135, issue 10, pp. 2496-2511, 2010.

[8] Avinash Bajaj, Oscar R. Miranda, Ronnie Phillips, Ik-Bum Kim, Joseph Jerry, Uwe Bunz and Vincent M. Rotello, "Array-Based Sensing of Normal, Cancerous, and Metastatic Cells Using Conjugated Fluorescent Polymers," Journal of the American Chemical Society, Vol. 132, Issue. 3, pp. 1018-1022, 2010.

[9] Sandipan Ray, Gunjan Mehta and Sanjeeva Srivastava, "Label-free detection techniques for protein microarrays: Prospects, merits and challenges," Proteomics, Vol. 10, Issue 4, pp. 731-748, 2010.

[10] Haowen Huang, Shaowen Huang, Shishan Yuan, Caiting Qu, Yi Chen, Zhongjian Xu, Bo Liao, Yunlong Zeng, and Paul K. Chu, "High-sensitivity biosensors fabricated by tailoring the localized surface plasmon resonance property of core-shell gold nanorods," Analytica Chimica Acta, Vol. 683, Issue. 2, pp. 242-247, 2011.

[11] Guanghua Wu, Ram H. Datar, Karolyn M. Hansen, Thomas Thundat, Richard J. Cote and Arun Majumdar, "Bioassay of prostate-specific antigen (PSA) using microcantilevers," Nature Biotechnology, VOl. 19, issue. 9, pp. 856-860, 2001.

[12] Gajendra Shekhawat, Soo-Hyun Tark, and Vinayak P. Dravid, "MOSFET-Embedded Microcantilevers for Measuring Deflection in Biomolecular Sensors," Science, Vol. 311, Issue. 5767, pp. 1592-1595, 2006.

[13] M. Calleja, M. Nordstrom, M. A lvarez, J. Tamayo, L. M. Lechuga, and A. Boisen, "Highly sensitive polymer-based cantilever-sensors for DNA detection," Ultramicroscopy Vol. 105, pp. 215-222, 2005.

[14] A. Johansson, M. Calleja, P. A. Rasmussen and A. Boisen, "SU-8 cantilever sensor system with integrated readout," Sensors and Actuators A, Vol. 123-124, pp. 111-115, 2006.

[15] Robert J. Chen, Sarunya Bangsaruntip, Katerina A. Drouvalakis, Nadine Wong Shi Kam, Moonsub Shim, Yiming Li, Woong Kim, Paul J. Utz, and Hongjie Dai, "Noncovalent functionalization of carbon nanotubes for highly specific electronic biosensors," Proceedings of National Academy of Science, Vol. 100, no. 9, pp. 4984-4989, 2003.

[16] Robert J. Chen, Hee Cheul Choi, Sarunya Bangsaruntip, Erhan Yenilmez, Xiaowu Tang, Qian Wang, Ying-Lan Chang, and Hongjie Dai, "An Investigation of the Mechanisms of Electronic Sensing of Protein Adsorption on Carbon Nanotube Devices," Journal of American Chemical Society, Vol. 126, pp. 1563-1568, 2004.

[17] Fernando Patolsky, Amir Lichtenstein, and Itamar Willner, "Detection of single-base DNA mutations by enzyme-amplified electronic transduction," Nature Biotechnology, Vol. 19, pp. 253-257, 2001.

[18] Rong Fan, Ophir Vermesh, Alok Srivastava, Brian K H Yen, Lidong Qin, Habib Ahmad, Gabriel A Kwong, Chao-Chao Liu, Juliane Gould, Leroy Hood & James R Heath, "Integrated barcode chips for rapid, multiplexed analysis of proteins in microliter quantities of blood," Nature Biotechnology, Vol. 26, no. 12, pp. 1373-1378, 2008.

[19] Gengfeng Zheng, Fernando Patolsky, Yi Cui, Wayne U Wang and Charles M Lieber, "Multiplexed electrical detection of cancer markers with nanowire sensor arrays," Nature Biotechnology, Vol. 23, no. 10, pp. 1294-1301, 2005.

[20] Y I Kim, T S Park, J H Kang, M C Lee, J T Kim, J H Park and H K Baik, "Biosensors for label free detection based on RF and MEMS technology," Sensors and Actuators B, Vol. 119, pp. 592-599, 2006.

[21] Claire Dalmay, Arnaud Pothier, Pierre Blondy, Mathilde Cheray, Fabrice Lalloue and Marie-Odile Jauberteau, "RF biosensor based Microwave filter for biological characterisation," in Proc. 39th European Microwave Conference," pp. 41-44, 2009.

[22] Gabriel M. Rebeiz and Jeremy B. Muldavin, "RF MEMS Switches and Switch Circuits," IEEE Microwave Magazine, Vol. 2, Issue. 4, pp. 59-71, 2001.

[23] Cristiano Palego, Jie Deng, Zhen Peng, Subrata Halder, C. M. Hwang, David I. Forehand, Derek Scarbrough, Charles L. Goldsmith, Ian Johnston, Suresh K. Sampath, and Arindom Datta, "Robustness of RF MEMS Capacitive Switches With Molybdenum Membranes," IEEE Transactions on Microwave Theory and Techniques, Vol. 57, No. 12, Dec. 2009.

[24] F. M. Guo, Z. Q. Zhu, Y. F. Long, W. M. Wang, S. Z. Zhu, Z. S. Lai, N. Li, G. Q. Yang, W. Lu, "Study on low voltage actuated MEMS RF capacitive switches," Sensors and Actuators A, Vol. 108, pp. 128-133, 2003.

[25] A. Gopinath, "Losses in Coplanar Waveguides," IEEE Transactions on Microwave Theory and Techniques, Vol. MTT-30, no. 7, 1982.

[26] Maria Tenje, Stephan Keller, Soren Dohn, Zachary J. Davis, and Anja Boisen, "Drift study of SU8 cantilevers in liquid and gaseous environments," Ultramicroscopy, Vol. 110, pp. 596-598, 2010.

[27] Z. Jamie Yao, Shea Chen, Susan Eshelman, David Denniston, Chuck Goldsmish, "Micromachined low-loss microwave switches," IEEE Journal on Microelectromechanical Systems, Vol. 8, no. 2, pp. 129-134, 1999.

[28] D. Roy Choudhary and Shail B. Jain, Linear Integrated Circuits, New Age International Pvt. Ltd., 2nd Edition, 2003.

[29] Yuan-Cheng Fung, "Stochastic flow in capillary blood vessels," Microvascular Research, Vol. 5, pp. 34-48, 1973.

[30] K. Svanes and B. W. Zweifach, "Variations in small blood vessel hematocrits produced in hypothermic rates by micro-occlusion," Microvascular Research, Vol. 1, pp. 210-220, 1968.

[31] Sung Yang, Akif Undar and Jeffery D. Zahn, "A microfluidic device for continuous, real time blood plasma separation," Lab on a Chip, Vol. 6, pp. 871-880, 2006.

The foregoing detailed description of the present invention is provided for purposes of illustration and is not intended to be exhaustive or to limit the invention to the embodiments disclosed, the scope of the invention limited only the claims hereto.

What we claim is:

1. An RF MEMS based biosensor with two sensing modes comprising:
   a) a non conductive substrate;
   b) parallel, spaced-apart electrically conductive ground lines situated atop said substrate;
   c) a bottom electrode comprising a conductive signal line positioned between said spaced-apart ground lines, said signal line aligned in parallel to said ground lines;
   d) a dielectric layer which covers said signal line;
   e) a top electrode comprising a flexible rectangular membrane having a top surface and a bottom surface, said membrane suspended above a portion of said dielectric layer covered signal line so as to define a gap between them, said flexible membrane at each end supported by and in electrical contact with said spaced apart ground lines; and,
   f) a coating of biorecognition elements disposed on said dielectric layer covered signal line, and the top surface of said flexible membrane.

2. The sensor of claim 1 wherein the biorecognition elements comprise immobilized antibodies.

3. The sensor device of claim 2 wherein immobilized antibodies are further disposed over the exposed surfaces of both the ground and signal lines.

4. The sensor of claim 1 wherein the flexible membrane is made of aluminum.

5. The sensor of claim 1 wherein the signal line is disposed equidistant between said ground lines.

6. The sensor of claim 4 wherein the flexible membrane is disposed perpendicularly to said signal line.

7. A multiplexed biosensor array for biodetection comprising:
   a) a multiplicity of RF MEMS sensor devices integrated into microfluidic channels of a microfluidic chip, said sensor devices arranged in a matrix of rows and columns, wherein each sensor device comprises:
      (1) a non conductive substrate;
      (2) parallel, spaced-apart electrically conductive ground lines situated atop said substrate;
      (3) a bottom electrode comprising a conductive signal line positioned between said spaced-apart ground lines, said signal line aligned in parallel to said ground lines;
      (4) a dielectric layer which covers said signal line;
      (5) a top electrode comprising a flexible rectangular membrane having a top surface and a bottom surface, said membrane suspended above at least a portion of said dielectric layer covered signal line so as to define a gap between them, said flexible membrane at each end supported by, and in electrical contact with said spaced apart ground lines; and,
      (6) a coating of biorecognition elements disposed on said dielectric layer covered signal line, exposed ground lines, and the top surface of said flexible membrane; and, wherein,
   b) each of the sensor devices in a given column are immobilized with the same biorecognition element;

c) each of said sensor devices within a given row are immobilized with different type of biorecognition element; and, d) each of the RF MEMS sensor devices in a given row are in fluidic contact with the same microfluidic channel, and each of the RF MEMS sensor devices in a given column are in parallel microfluidic channels.

8. The multiplexed sensor array of claim 7 wherein the biorecognition element comprises immobilized antibodies.

\* \* \* \* \*